United States Patent [19]

Holladay

[11] 4,188,097
[45] Feb. 12, 1980

[54] METHOD OF AND APPARATUS FOR TESTING VISUAL INTEGRITY

[76] Inventor: Jack T. Holladay, 8484 Ariel, Houston, Tex. 77074

[21] Appl. No.: 802,648

[22] Filed: Jun. 2, 1977

[51] Int. Cl.$^2$ .............................................. A61B 3/02
[52] U.S. Cl. ....................................... 351/36; 351/35; 351/25; 351/17
[58] Field of Search ...................... 351/25, 17, 36, 18, 351/28, 29, 35

[56] References Cited

U.S. PATENT DOCUMENTS

| | | | |
|---|---|---|---|
| 2,294,382 | 9/1942 | Burian | 351/25 |
| 3,205,505 | 9/1965 | Fletcher et al. | 351/32 |
| 3,801,188 | 4/1974 | Hunt et al. | 351/36 |

OTHER PUBLICATIONS

Flynn et al., Brightness Matching in Strabismic Amblyopia.
Burian et al., Binocular Vision and Ocular Motility, 1974.
Eastman et al., Instrument with Variable Beam Splitter, for Measuring Contrast Sensitivity.
Luminance, Contrast Function and Visual Acuity in Functional Amblyopia, Lawwill et al.
Gunkel et al., Colorimetry by a New Principle, 2/78.

*Primary Examiner*—John K. Corbin
*Assistant Examiner*—Rodney B. Bovernick
*Attorney, Agent, or Firm*—Bernard A. Reiter

[57] ABSTRACT

A method of and apparatus for determining the visual integrity of an individual is disclosed. An equal amount of visible light intensity is provided to the right and left eyes by viewing a target through a binocular viewing mechanism. The eyes of the individual are adapted to the equal intensities of light for an adaptation period and the individual then adjusts the light intensity until the perceived light intensity in each eye is equal. The difference between the light intensities provided to the right and left eyes are measured, which provides an indication of the visual integrity of the individual.

18 Claims, 4 Drawing Figures

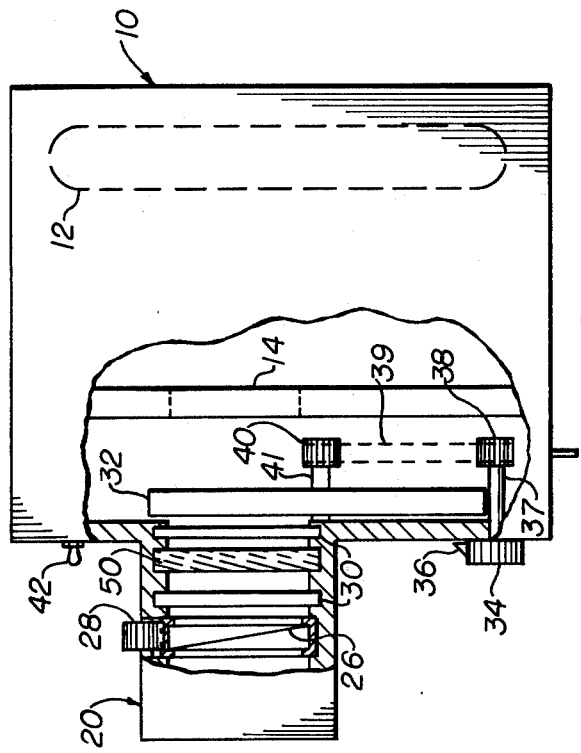
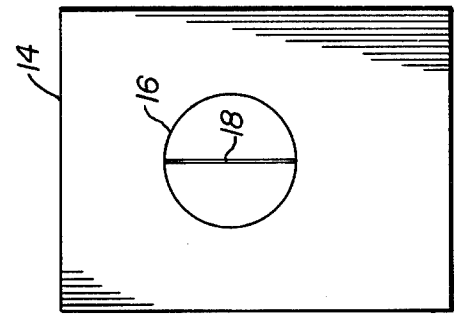
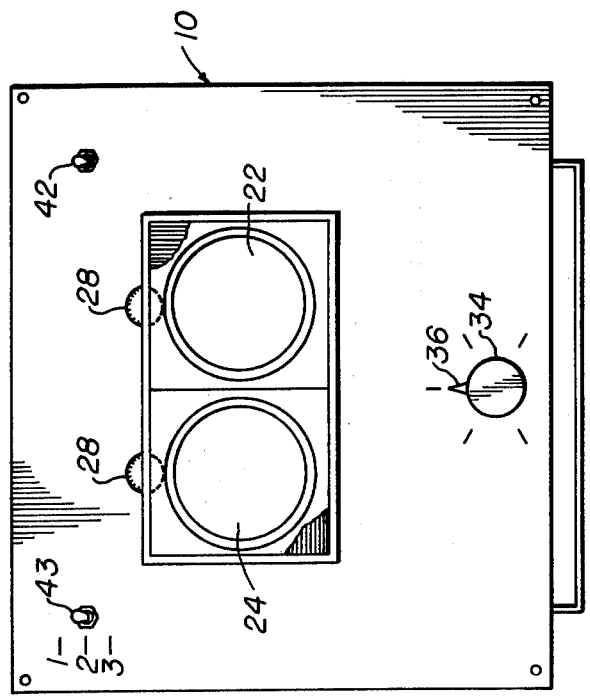
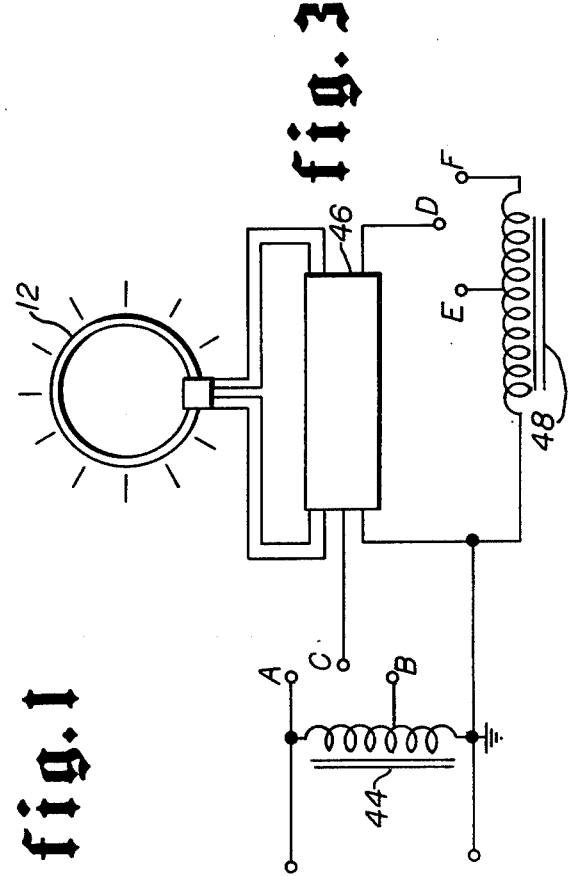

METHOD OF AND APPARATUS FOR TESTING VISUAL INTEGRITY

BACKGROUND OF THE INVENTION

For many years, the eyes of an individual have been tested to discover visual deficiencies. However, no accurate repeatable tests have been suggested for determining the visual integrity of the individual's eyes. That is, no accurate repeatable tests have been suggested to measure the functioning of the retina, the optic nerves, optic radiations and the occiptial lobes. The necessity of such a test is important in several areas. For instance, such testing is necessary to determine whether the individual has an optic nerve dysfunction. Also, such testing is necessary to make a diagnosis or determination of a disease where temporal variations in the course of the disease is an important factor, such as in the determining whether the individual is sufffering from ischemic optic neuropathy or from multiple schlerosis. Moreover, such testing is necessary as an aid in determining the effectiveness of the therapy once the disease is diagnosed.

It has been suggested that amblyopia in certain individuals could be a measurement of visual integrity. This utilizes a device for providing a single light base level to one eye. A neutral density optical wedge was positioned in front of the opposite eye to vary the light intensity in that eye. The individual then moved the neutral density optical wedge to a position where the perceived light was of equal intensity. The results obtained, however, were confusing. It is believed these confusing results were caused because the eyes of the individual were not permitted to adjust to an equal amount of light intensity prior to the adjustment made with the wedge. Further, this apparatus was quite expensive and difficult to use.

Accordingly, it is an object of this invention to provide a method of and apparatus for testing the visual integrity of an individual in an accurate, effective and repeatable manner.

Further, it is an object of the present invention to provide a method of an apparatus for testing the visual integrity of an individual to determine optic nerve dysfunction by providing light to the eyes in wavelengths of blue, red, yellow and green.

Further, it is an object of the invention to provide a method of and apparatus for testing the visual integrity of an individual at three intensity levels in order to place the eyes in scotopic, mesopic and photopic conditions.

In accordance with the invention, a method of and apparatus for testing the visual integrity of an individual is provided. Initially an equal amount of visible light intensity is provided to the right and left eye of the individual by illuminating a target with equal light intensity and having the individual view the target through a binocular viewing mechanism to provide orthophoric viewing. The eyes of the individual are adapted to the equal intensities for an adaptation period. The individual then adjusts the light intensity in both eyes until the perceived light is equal. A measurement is then made of the difference between the light intensity provided at the right eye and the light intensity provided at the left eye as an indication of the visual integrity of the individual's right eye compared to the left eye.

DESCRIPTION OF THE DRAWINGS

Other objects and advantages of the invention will become apparent upon reading the following detailed description and upon reference to the drawings, in which:

FIG. 1 is a front elevational view, partly in section, of apparatus constructed according to the present invention to test the visual integrity of an individual.

FIG. 2 is a side elevational view, partly in section, of the embodiment illustrated in FIG. 1.

FIG. 3 is a schematic illustration of a wiring diagram usable with the light source in the embodiment of the invention illustrated in FIGS. 1 and 2.

FIG. 4 is a front elevational view of a target usable with the embodiment of the invention illustrated in FIGS. 1 and 2.

While the invention will be described in connection with a preferred embodiment and procedure, it will be understood that it is not intended to limit the invention to that embodiment and procedure. On the contrary, the following description is intended to be illustrative of an exemplary form of the invention and therefore the claims appended hereafter shall be interpreted to cover and define the varying alternatives, modifications and equivalents as may be included within the spirit and scope thereof.

DESCRIPTION OF THE INVENTION

Turning now to FIGS. 1 and 2, the preferred apparatus used to test the visual integrity of an individual employs a housing 10. A light source 12, used to illuminate a target and which is preferably a circular fluorescent type emitting diffused light, such as sold by General Electric with Model No. FC8T9-CW-RS, is positioned towards the back and within housing 10. A translucent sheet of material 14 is then provided in front of light 12 for further diffusing light passing from light source 12 and illuminating target 16. Target 16 is provided on material 14 for viewing from the front of housing 10 and has a line 18 vertically bisecting it, as shown in FIG. 3.

The target is viewed through a binocular viewing mechanism 20, which extends outwardly from the front of housing 10. Binocular mechanism 20 is used to provide an orthophoric view of the target to the individual. A Cyclopean axis passes through the geometric center of target 16. The binocular mechanism has a right eyepiece 22 for viewing substantially one-half of target 16 formed when bisecting the target with a sagittal plane passing through the Cyclopean axis and a left eyepiece 24 for viewing substantially the other half of target 16. Each eyepiece includes a pair of Risley prisms 26 and associated adjustment mechanism 28 to aid the individual in obtaining an orthophoric view of target 16. It has been found that best results are obtained by causing the view from eyepice 22 and 24 to overlap line 18 slightly.

A mechanism is provided in each eyepiece 22 and 24 to vary the intensity of light arriving at the respective eyepiece. This is preferably accomplished by using a pair of fixed plane polarizers 30 for each eyepiece and a plane polarizer 32 movable relative to each pair of fixed polarizers 30. The pair of plane polarizers 30 fixed between right eyepiece 22 and target 16 are used to provide light with a first polarization axis at the right eyepiece 22 and the pair of plane polarizers 30 fixed between left eyepiece 24 and target 16 are used to provide light with a second polarization axis at left eyepiece 24.

The first and second polarization axes are fixed with one axis lying parallel to the sagittal plane, such as shown for right eyepiece 22 in FIG. 1, and one axis lying at a right angle, such as shown for left eyepiece 24. Movable plane polarizer 32 is rotatably mounted about the Cyclopean axis to rotate the polarization axis relative to the first and second polarization axes. Thus, the light intensity at one eyepiece increases and the intensity at the other eyepiece decreases by rotating movable polarizer 32. Preferably, equal light intensity is provided at the right and left eyepieces when the polarization axis bisects the angle formed by the first and second axes or at 45° to the sagittal plane.

The difference between the light intensity provided at right eyepiece 22 and left eyepiece 24 is determined by using a control knob 34 with an associated pointer 36 positioned on the front of housing 10. Knob 34 is connected by an appropriate apparatus to the mechanism for varying the light intensity to each eyepiece. Preferably, knob 34 is connected to shaft 37 having drive pulley 38 connected thereto. A drive chain 39 extends between drive pulley 38 and pulley 40 joined to axle 41 supporting movable polarizer 32 at its rotating axis. Thus, the light intensity at each eyepiece is varied by the individual rotating knob 34 with pointer 36 indicating a measurement of the difference of these intensities.

Light source 12 is activated by an on/off switch 42 positioned on the front of housing 10 for testing the visual integrity of an individual. However, in certain testing, such as testing for retinal or optic nerve dysfunction, it is desired to test the visual integrity of the individual at different light intensity levels. Preferably, the number of light levels provided is three and these levels are such as to cause the eyes of the individual to be placed in scotopic, mesopic and photopic conditions. As best seen in FIG. 3, this may be accomplished by using a double pole three position switch 43 for controlling an inductor 44 lying in parallel with a ballast 46 for lamp 12 and an inductor 48 lying in series with ballast 46. An example of such a switch 43 is sold by Alco with Model No. MTA206PA and of such inductors 44 and 48 is sold by General Electric, with Model No. 9T92A1. Ballast 46 is, preferably, a trigger model, such as that sold by General Electric Model No. 6G3795A. It was found that the scotopic condition may be obtained by switching across the points B-C of inductor 44 and across points D-F of inductor 48. The mesopic condition may be obtained by switching across points B-C of inductor 44 and across points D-E of inductor 48. A photopic condition may be obtained by switching across points A-C of inductor 44 and across points D-E of inductor 48.

Moreover, the tests of the visual integrity for certain types of visual disorders require the use of visible light in wavelengths of blue, red, yellow and green. For instance, in testing the individual for optic nerve dysfunction, individuals having such disorder usually have a problem in the red wavelength. A colored filter 50 is, therefore, located between eyepieces 22 and 24 and target 16 to test for such disorders, namely, optic nerve dysfunction.

In operation, switch 42 is moved to the "on" position, thereby causing lamp 12 to emit light. Switch 43 is moved to one of the three intensity levels desired for testing the individual and control knob 34 is positioned so that equal amounts of light intensity are provided at light target 16 and to right eyepiece 22 and left eyepiece 24. The individual then looks through eyepiece 22 and 24, adjusts prisms 26 for each eye to provide an orthophoric view of target 16 to the individual. Preferably, a slight amount of overlap of line 18 occurs in each eyepiece to prevent the takeover by a dominant eye of the individual which would cause confusing results. The individual then adapts the eyes to the equal light intensity by looking at the equal intensities for a period of time, perhaps 30 seconds, or by closing the eyes and then looking at target 16. The individual then adjusts the light intensity in both eyes by rotating knob 34 until the light perceived by each eye is equal. The position of pointer 36 is then noted, which provides a comparison of the amount of light perceived in the right eye with the amount of light perceived in the left eye. This comparison provides an indication of the relative visual integrity between the two eyes of the individual being tested. When desired, these steps are repeated at each level of the three light intensities. Preferably, a color filter 46 is positioned between eyepieces 22 and 24 and target 16 to test the individual's reactions under color conditions. Most preferred, this filter is changed to provide wavelengths of blue, red, yellow and green for testing of retinal and optic nerve dysfunction.

That which is claimed and desired to be secured by United States Letters Patent is:

1. A method of determining the visual integrity of an individual's eyes by comparing the brightness perceived in the right eye with the brightness perceived in the left eye, comprising:
    providing an equal amount of visible light intensity to the right and left eye of the individual;
    instructing the individual to adapt his eyes to the equal intensities during an adaptation period;
    instructing the individual to adjust the light intensity until the perceived light intensity is equal in both eyes;
    measuring the difference between the light intensity provided at the right eye and the light intensity provided at the left eye after the individual has adjusted the light intensities so as to obtain a comparison of the brightness perceived in the right eye with the brightness perceived in the left eye and thus obtain a quantitative indication of the visual integrity of the individual's right eye compared to the left eye.

2. The method of claim 1, including providing the equal amount of light to both eyes at three levels of intensity to place the eyes in scotopic, mesopic and photopic conditions.

3. The method of claim 1, including varying the wavelength of the visible light to permit testing in wavelengths of blue, red, yellow and green to test for optic nerve dysfunction.

4. Apparatus used to test the visual integrity of an individual, comprising:
    a target;
    a light source for illuminating the target;
    a binocular viewing mechanism or providing an orthophoric view of the target to the individual with a Cyclopean axis extending through the geometric center of the target, said binocular viewing mechanism having a right eyepiece for viewing substantially one-half of the target formed when bisecting the target with a sagittal plane passing through the Cyclopean axis and a left eyepiece for viewing substantially the other half of the target;
    means for varying the intensity of light arriving at the right and left eyepiece in response to the light intensity perceived in each eye by the individual until the light intensity is perceived to be equal in both eyes; and means connected to said varying means for providing a measurement of the difference between the light intensity provided at the right eyepiece and the light intensity provided at the left eyepiece as an indication of the visual integrity of the individual.

5. The apparatus of claim 4, wherein said varying means includes a pair of plane polarizers fixed between the right eyepiece and said target to provide polarized light with a first axis at the right eyepiece, a pair of plane polarizers fixed between the left eyepiece and said target to provide polarized light with a second axis at the left eyepiece, the first and second axes being at right angles with one axis lying parallel to the sagittal plane and a plane polarizer rotatably mounted about the Cyclopean axis to rotate the polarization axis relative to the first and second polarization axes to cause the light intensity at one eyepiece to increase while decreasing the light intensity at the other eyepiece.

6. The apparatus of claim 5, wherein said measuring means is connected to the rotatable plane polarizer.

7. The apparatus of claim 5, wherein the rotatable plane polarizer is positioned to provide equal light intensity at the right and left eyepiece when the polarization axis bisects the angle formed by the first and second axes.

8. The apparatus of claim 4, wherein a line is located on and bisects said target along the sagittal plane.

9. The apparatus of claim 4, including means adjusting said light source to provide three light intensity levels to place the eyes in scotopic, mesopic and photopic conditions.

10. The apparatus of claim 4, wherein said target is a light diffusing partition with the light being received from the light source on the back and viewed through the binocular viewing mechanism on the front.

11. The apparatus of claim 4, including a color filter positioned across the right and left eyepiece for testing in selected color wavelengths.

12. The apparatus of claim 4 wherein the means for varying the intensity of light arriving at the right and left eyepiece is accomplished by polarization.

13. A method of testing the visual integrity of an individual's eyes by comparing the brightness perceived in the right eye with the brightness perceived in the left eye, comprising:

a target with a uniform light intensity;

visually bisecting the target by passing a sagittal plane through a Cyclopean axis which extends through the geometrical center of the target with substantially one-half of the target being viewed through a right eyepiece of a binocular mechanism and substantially the other half being viewed through a left eyepiece of the binocular mechanism;

causing the individual to adjust the light intensities from the target when viewed through the binocular mechanism until the light perceived by the right eye is equal to the light perceived by the left eye;

measuring the difference between the light intensity provided at the right eyepiece and the light intensity provided at the left eyepiece to obtain a comparison of the brightness perceived in the right eye with the brightness perceived in the left eye as an indication of the visual integrity of the individual's right eye compared to the left eye.

14. The method of claim 13, including providing the levels of visible light intensity to the target to place the eyes of the individual in scotopic, mesopic and photopic conditions.

15. The method of claim 13, including varying the wavelength of the visible light at the eyepiece to permit testing in wavelengths of blue, red, yellow and green to test for retinal and optic nerve dysfunction.

16. A method of determining the visual integrity of an individual's eyes by comparing the brightness perceived in the right eye with the brightness perceived in the left eye, comprising:

providing an equal amount of light to both eyes at three levels of intensity to place the eyes in scotopic, mesopic and photopic conditions;

instructing the individual to adapt his eyes to the equal intensities during an adaptation period;

instructing the individual to adjust the light intensity until the perceived light intensity is equal in both eyes;

measuring the difference between the light intensity provided at the right eye and the light intensity provided at the left eye after the individual has adjusted the light intensities so as to obtain a comparison of the brightness perceived in the right eye with the brightness perceived in the left eye and thus obtain a quantitative indication of the visual integrity of the individual's right eye compared to the left eye.

17. The method of claim 16, including varying the wave length of a visible light to permit testing in wave lengths of blue, red, yellow and green to test for optic nerve dysfunction.

18. A method of determining the visual integrity of an individual's eyes by comparing the brightness perceived in the right eye with the brightness perceived in the left eye, comprising:

providing an equal amount of light to both eyes at three levels of intensity to place the eyes in scotopic, mesopic and photopic conditions;

instructing the individual to adapt his eyes to the equal intensities during an adaptation period preceding the intensity changes;

instructing the individual to adjust the light intensity until the perceived light intensity is equal in both eyes, including varying the wave length of the visable light to permit testing in wave lengths of blue, red, yellow and green to test for optic nerve dysfunction;

measuring the difference between the light intensity provided at the right eye and the light intensity provided at the left eye after the individual has adjusted the light intensities so as to obtain a comparison of the brightness perceived in the right eye with the brightness perceived in the left eye and thus obtain a quantitative indication of the visual integrity of the individual's right eye compared to the left eye.

* * * * *